United States Patent [19]

Wilk et al.

[11] Patent Number: 5,037,433

[45] Date of Patent: Aug. 6, 1991

[54] ENDOSCOPIC SUTURING DEVICE AND RELATED METHOD AND SUTURE

[76] Inventors: Peter J. Wilk, 185 W. End Ave., New York, N.Y. 10023; David Sekons, 455 E. 86th St., New York, N.Y. 10028

[21] Appl. No.: 525,253

[22] Filed: May 17, 1990

[51] Int. Cl.[5] ............................................. A61B 17/00
[52] U.S. Cl. .................................. 606/139; 606/144; 606/222
[58] Field of Search ............... 606/139, 144, 147, 148, 606/219, 222

[56] References Cited

U.S. PATENT DOCUMENTS

| | | | |
|---|---|---|---|
| 4,164,225 | 8/1979 | Johnson et al. | 606/146 |
| 4,485,816 | 12/1984 | Krumme | 606/219 |
| 4,493,323 | 1/1985 | Albright et al. | 606/144 |
| 4,841,888 | 6/1989 | Mills et al. | 112/169 |
| 4,923,461 | 5/1990 | Caspari et al. | 606/148 |
| 4,926,860 | 5/1990 | Stice et al. | 606/144 |
| 4,935,027 | 6/1990 | Yoon | 606/148 |
| 4,968,315 | 11/1990 | Gatturna | 606/139 |

Primary Examiner—Stephen C. Pellegrino
Assistant Examiner—Gary Jackson
Attorney, Agent, or Firm—R. Neil Sudol; Henry D. Coleman

[57] ABSTRACT

An endoscopic suturing device comprises an endoscope and a needle having a spring bias construction tending to bend the needle into an arcuate configuration. The endoscope includes an elongate flexible outer tubular member and a biopsy channel extending longitudinally through the tubular member. A flexible inner tubular member is disposed inside the biopsy channel of the outer tubular member, while the needle is disposed in a straightened configuration at least part partially inside the inner tubular member at a distal end thereof. The surgical instrument further comprises an ejector device in the form of an elongate flexible rod member slidably disposed inside the inner tubular member proximally of the needle for ejecting the needle from the inner tubular member. A suture is provided with an end attached to a proximal end of the needle, while a closure device in the form of a forceps is provided for closing the suture upon an ejection of the needle from the biopsy channel by a distally directed motion of the rod member and a subsequent assumption by the needle of the arcuate configuration.

51 Claims, 6 Drawing Sheets

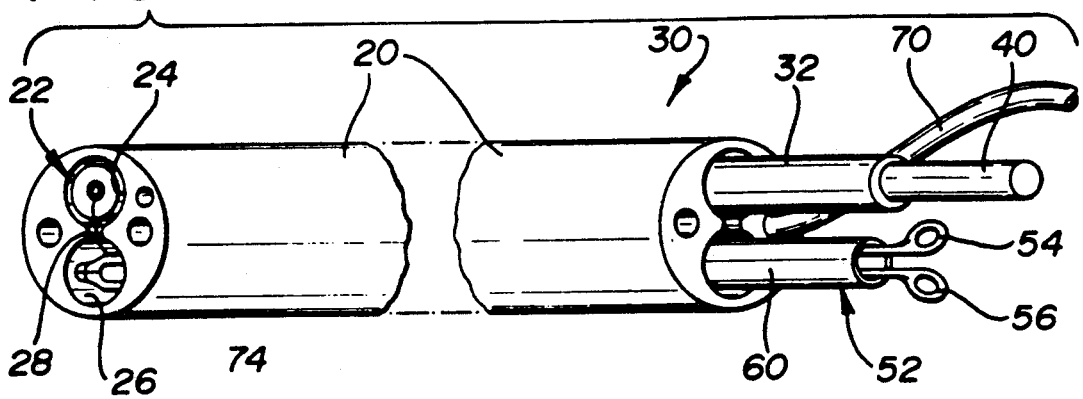
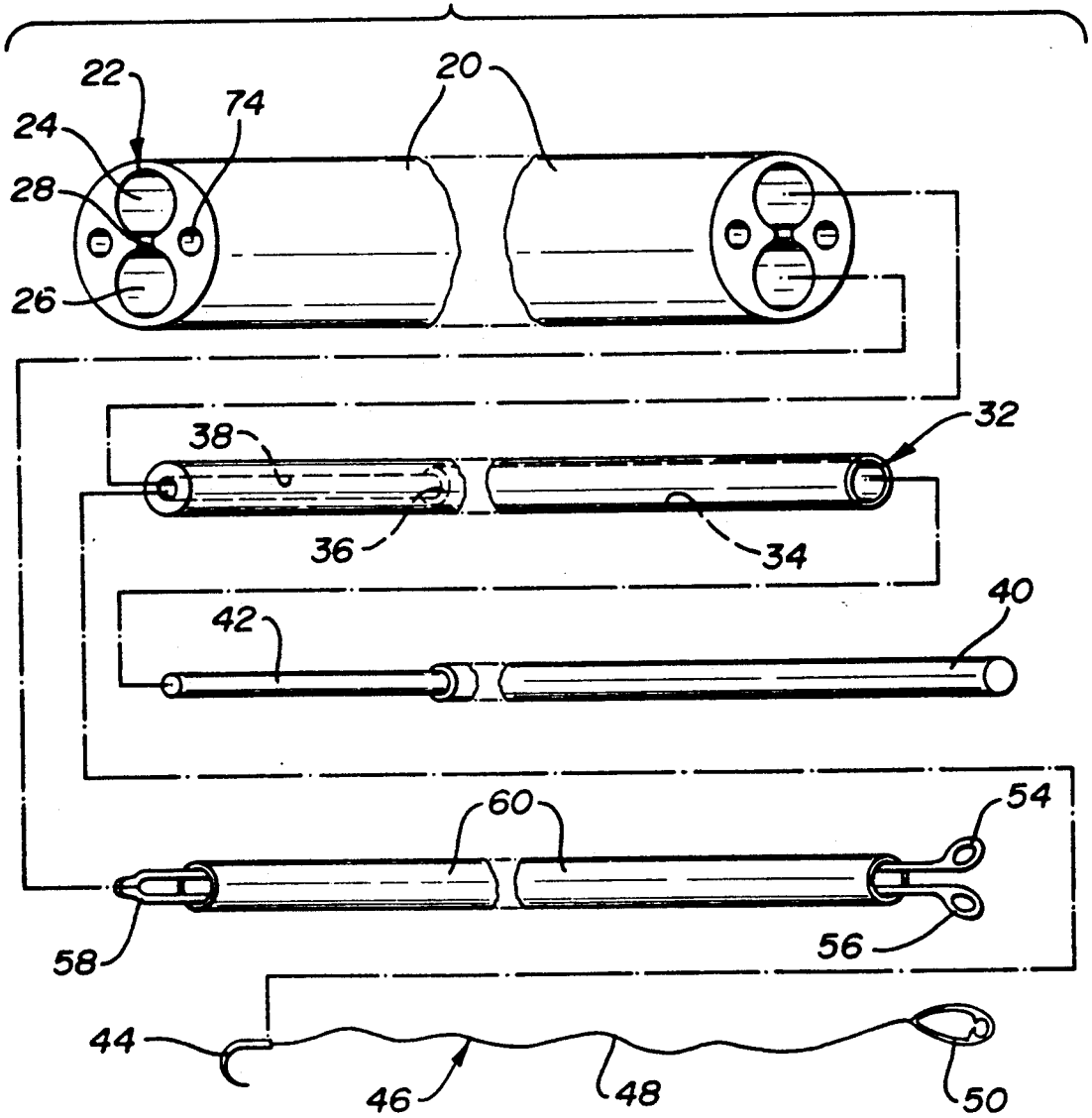

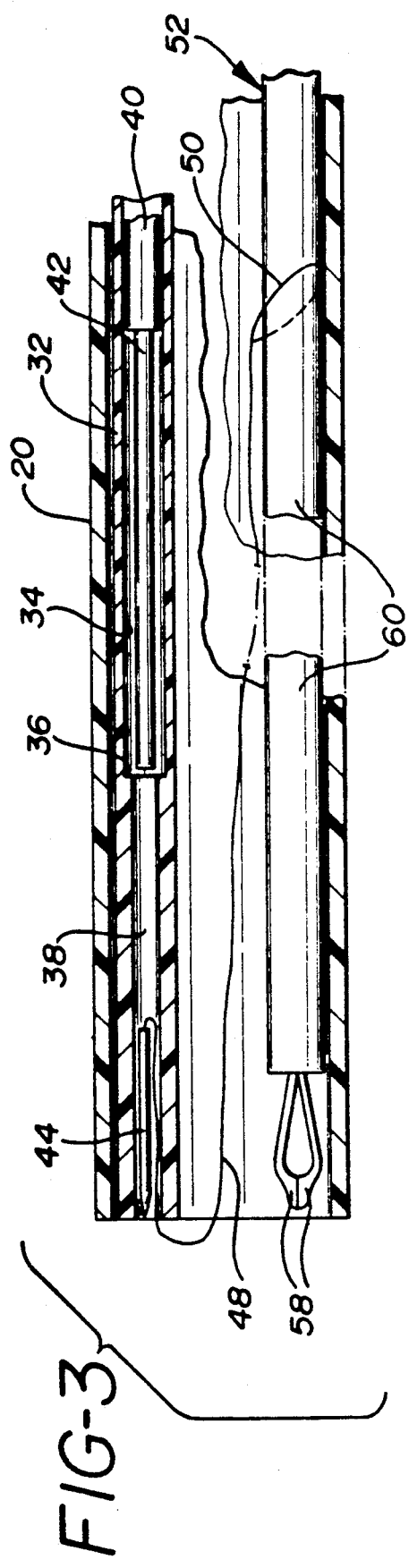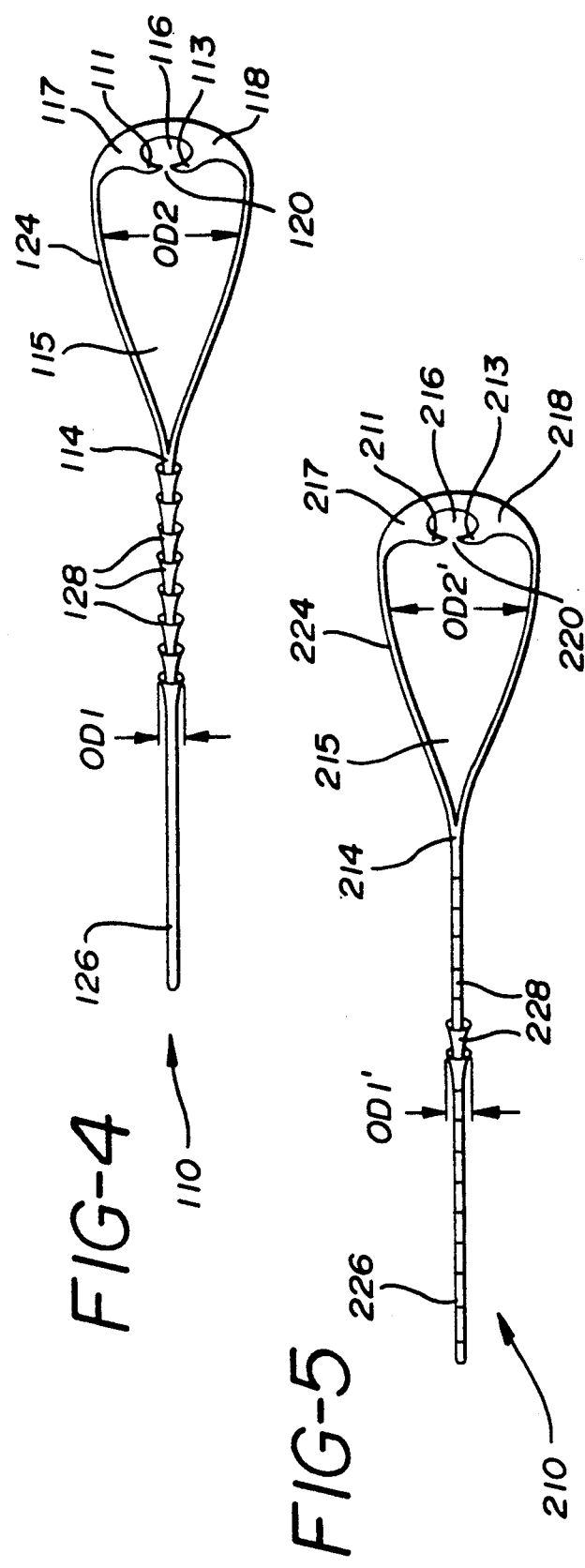

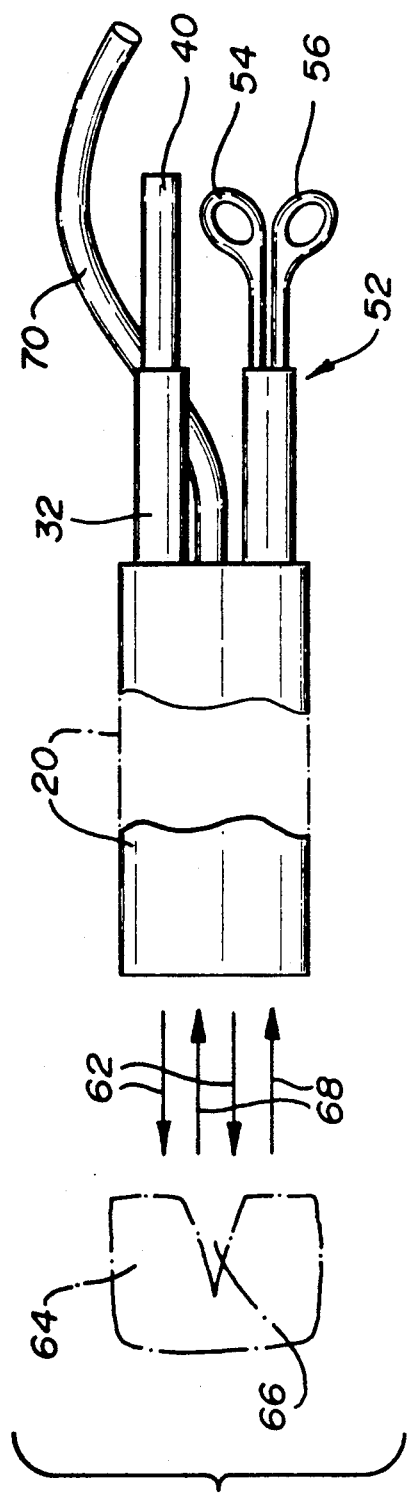
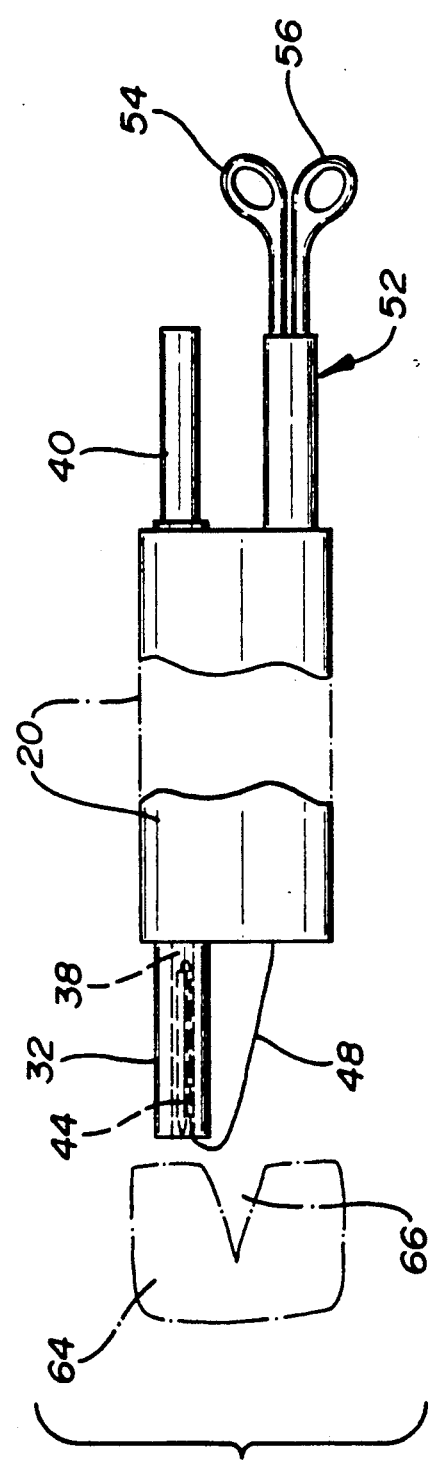

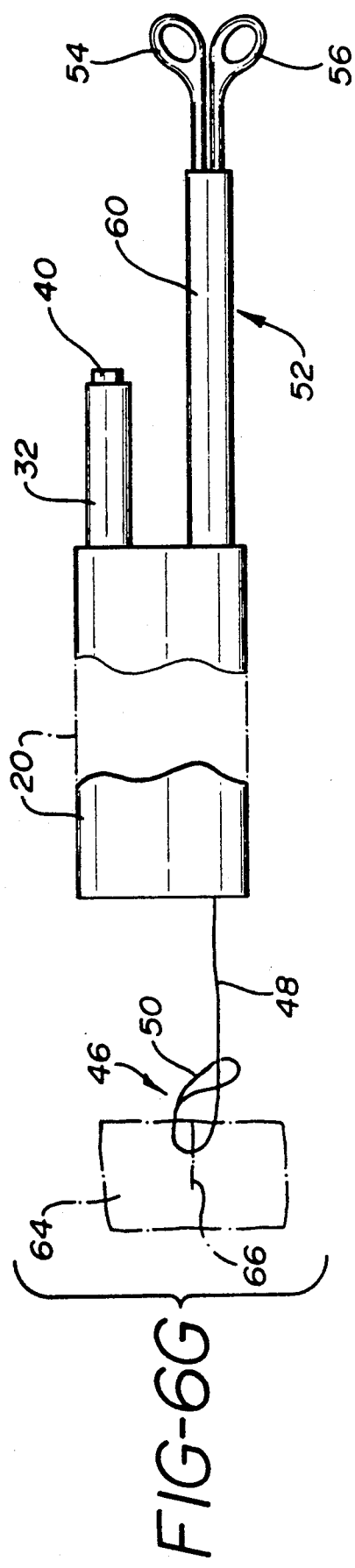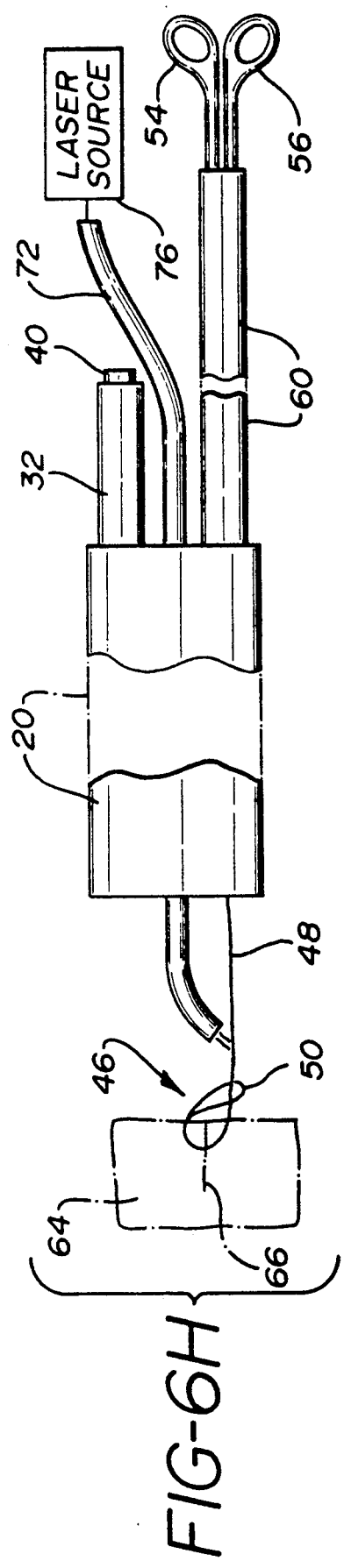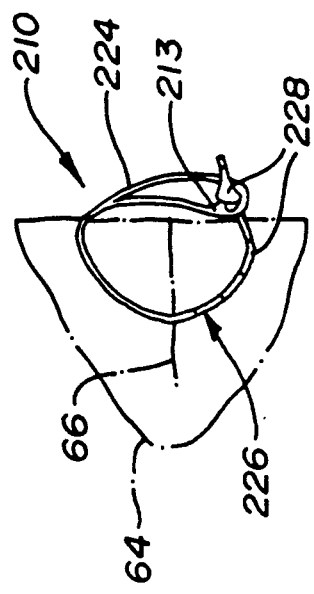

ENDOSCOPIC SUTURING DEVICE AND RELATED METHOD AND SUTURE

BACKGROUND OF THE INVENTION

This invention relates to an endoscopic suturing device. More particularly, this invention relates to a device usable with an endoscope for performing a sewing or stitching operation on a patient's internal body tissues at a surgical site not visible to the unaided eye. This invention also involves a surgical procedure utilizing an endoscope. The invention further relates to a surgical suture and an associated needle both particularly adapted for use in a surgical procedure and an endoscopic stapling device in accordance with the invention.

Conventional surgical techniques for repairing tissue injuries such as hernias and perforated ulcers, for closing other openings in internal body tissues and for ligating tubular body organs such as sperm ducts and Fallopian tubes, generally require that an extensive incision be made in the patient's abdominal wall. Such an operation is generally traumatic to the patient, involves considerable surgeon time and requires a relatively lengthy convalescence. This is the case even though only one or a small number of sutures is required to repair the injury or tie off the vessel.

OBJECTS OF THE INVENTION

An object of the present invention is to provide a surgical procedure for closing openings internal to a patient's body, which is less invasive than conventional surgical closure methods.

Another object of the present invention is to provide such a surgical procedure which is quicker than conventional surgical procedures and which reduces the typical postoperative convalescence period.

A related object of the present invention is to provide an improved surgical closure procedure using an endoscope.

Another object of the present invention is to provide a suturing device usable with an endoscope.

An associated object of the present invention is to provide an endoscopic suturing device.

Another, more particular, object of the present invention is to provide a suture usable with such an endoscopic suturing device.

A further particular object of the present invention is to provide a surgical needle usable with such an endoscopic suturing device.

SUMMARY OF THE INVENTION

A surgical instrument comprises, in accordance with the present invention, an endoscope and a needle having a spring bias construction tending to bend the needle into an arcuate configuration. The endoscope includes an elongate flexible outer tubular member and a biopsy channel extending longitudinally through the tubular member, while the needle is disposed in a straightened configuration at least partially inside the biopsy channel at a distal end thereof. The surgical instrument further comprises an ejector device for ejecting the needle from the biopsy channel and a suture having an end attached to a proximal end of the needle A closure device is provided for closing the suture upon an ejection of the needle from the biopsy channel by a distally directed motion of the rod member and a subsequent assumption by the needle of the arcuate configuration.

In a preferred embodiment of the invention, the ejection device includes an elongate flexible rod member slidably disposed inside an elongate flexible inner tubular member in turn slidably disposed in the biopsy channel of the endoscope's outer tubular member. The needle is then disposed in a straightened configuration at least partially inside the inner tubular member distally of a distal end of the rod member.

Pursuant to another feature of the present invention, the closure device includes an elongate flexible forceps member slidably disposed in the endoscope.

In accordance with another feature of the present invention, the biopsy channel of the endoscope includes a pair of parallel elongate main channel portions communicating with one another along their lengths via an elongate connecting channel portion. The inner tubular member is slidably disposed in one of the main channel portions, while the rod member is slidably disposed inside the other main channel portion.

The suture includes a loop member traversed by the elongate flexible forceps member, the suture further including a thread member attached at one end to the needle and at an opposite end to the loop member. The thread member traverses the connecting channel portion of the biopsy channel.

Pursuant to another feature of the present invention, a locking device is provided for locking the suture upon closure thereof by the closure device. The locking device is essentially incorporated into the suture device and advantageously includes a series of projections provided along the thread member of the suture device and an aperture in the suture communicating with an opening defined by the loop member of the suture. Moreover, the thread member has an outer diameter defined by the projections, and the loop member's opening has a linear dimension substantially larger than the outer diameter of the thread member. The aperture has a linear dimension smaller than the outer diameter of the thread member, while the locking device further includes a part on the suture for preventing a removal of the thread member from the aperture upon a passing of the thread member through the loop member and a subsequent pulling of the thread member into the aperture from the loop member.

A severing device may be incorporated into the surgical instrument for cutting or severing a portion of the suture upon a closing thereof. The severing device may include a laser device with an optical fiber insertable through a longitudinal opening in said outer tubular member.

Pursuant to specific feature of the present invention, the rod member, the inner tubular member, the forceps member, and the main channel portions are all substantially cylindrical.

Pursuant to yet another specific feature of the present invention, an arrest is provided for preventing the rod member from moving more than a predetermined distance in a distal direction relative to the inner tubular member. In particular, the arrest includes a shoulder on the rod member engageable with a shoulder internal to the inner tubular member.

In accordance with a feature of the present invention, a surgical assembly comprises an elongate flexible tubular member, an elongate flexible rod member, a needle having a spring bias construction tending to bend the needle into an arcuate configuration, and a suture. The tubular member has a diameter sufficiently small so that the tubular member is slidably insertable into a biopsy channel extending longitudinally through a flexible tubular endoscope member. The rod member is slidably disposed inside the elongate flexible tubular member, while the needle is disposed in a straightened configuration at least partially inside the tubular member distally of a distal end of the rod member. The suture has an end attached to a proximal end of the needle. In addition, the assembly may include an elongate flexible forceps member for closing the suture upon an ejection of the needle from the tubular member by a distally directed motion of the rod member and a subsequent assumption by the needle of the arcuate configuration In that event, the suture includes a loop member traversed by the elongate flexible forceps member and further includes a thread member attached at one end to the needle and at an opposite end to the loop member.

A suture device in accordance with the present invention comprises a thread member, a loop member, a joint connecting the thread member to the loop member, a locking device or member, and a needle. The thread member is provided along at least a portion of its length with a series of resiliently collapsible projections, the thread member having an outer diameter defined by the projections. The loop member defines an opening having a linear dimension substantially larger than the outer diameter of the thread member. And either the joint or the loop member or both define at least in part an aperture having a linear dimension smaller than the outer diameter of the thread member and communicating with the opening defined by the loop. The locking device serves to prevent a removal of the thread member from the aperture upon a passing of the thread member through the loop member and a subsequent pulling of the thread member into the aperture from the loop member. The needle has a sharp end and is attached at an opposite end to a free end of the thread member. In addition, the needle has a spring bias construction tending to bend the needle into an arcuate configuration.

Preferably, the projections along the thread member are collapsible under force applied along the thread member in one direction and expandable under force applied along the thread member in an opposite direction. More preferably, the projections take the form of substantially hollow conical elements.

A method for performing a surgical operation on internal body tissues of a patient comprises, in accordance with the present invention, the steps of inserting a tubular endoscope member through an aperture in the patient's body, using the endoscope to visually locate the internal body tissues inside the patient's body, and upon locating the surgical site, pushing an elongate flexible rod member in a distal direction through a biopsy channel in the tubular endoscope member to eject a needle disposed in a straightened configuration inside the channel at a distal end of the tubular endoscope member. In this method, the needle has a spring bias construction tending to automatically bend the needle into an arcuate configuration, and the needle further has a proximal end attached to a suture. Upon ejection of the needle from the endoscope biopsy channel, the needle is passed in the arcuate configuration through the internal body tissues. After passing of the needle through the internal body tissues, the suture is closed, whereupon the tubular endoscope member is withdrawn or removed from the patient's body though the introduction aperture.

Pursuant to another feature of the present invention, the needle has a sharp end opposite its proximal end and the suture has a thread member and a loop member attached to the thread member at an end thereof opposite the needle. In accordance with this feature of the invention, the step of closing the suture comprises the steps of grasping the sharp end of the needle and pulling the needle and a portion of the thread member through the loop member. Preferably, the grasping of the sharp end of the surgical needle is accomplished with the aid of a forceps device, while pulling the needle and the thread member of the suture comprises the step of pulling a portion of the forceps device through the loop member of the suture. In another step, the suture is locked in a closed configuration upon a completed-pulling of the thread member through the loop member of the suture.

In accordance with the present invention, the aperture through which the endoscope is introduced into the patient may be a natural body opening or, alternatively, may be formed by piercing the patient's body, e.g., with a trocar.

An endoscopic suturing device in accordance with the present invention enables a non-invasive closure of internal openings and vessels. Accordingly, an internal closure operation performed in accordance with the present invention will greatly reduce the physical and emotional trauma that many patients undergo during surgery design to close internal wounds or ligate tubular body organs.

More specifically, using a procedure in accordance with the present invention, many surgical operations can be accomplished without the formation of any new opening in the external body tissues In such cases, the endoscopic suturing device is operated through a natural body aperture (the mouth or rectum). In other cases, the only opening which is needed is one just large enough to accommodate a fiber optic endoscope. Such an operation would be useful, for example, to repair hernias.

Use of an endoscopic suturing device in accordance with the present invention, therefore, minimizes operation time, as well as the hospital stay. Many patients can be therapeutically treated on an out-patient basis, thereby conserving valuable room space and other hospital facilities for patients whose injuries or illness absolutely requires invasive surgery.

A surgical instrument and technique in accordance with the present invention will serve to reduce hospitalization costs, as well as reduce complications attendant upon invasive surgical operations.

BRIEF DESCRIPTION OF THE DRAWING

FIG. 1 is a schematic partial side elevational view, on an enlarged scale, of an endoscopic suturing device in accordance with the present invention, showing distal and proximal ends of the suturing device bent outwardly from the plane of the paper.

FIG. 2 is a schematic exploded view, in side elevation, of the endoscopic suturing device of FIG. 1, various parts of the endoscopic suturing device being bent along central portions into the plane of the paper and at opposite ends out of the plane of the paper.

FIG. 3 is a schematic partial longitudinal cross-sectional view of the endoscopic suturing device of FIGS. 1 and 2, on an even larger scale.

FIG. 4 is a partial side perspective view, on an enlarged scale, of a suture utilizable in an endoscopic suturing device in accordance with the present invention.

FIG. 5 is a partial side perspective view, on an enlarged scale, of another suture utilizable in an endoscopic suturing device in accordance with the present invention.

FIGS. 6A through 6H are schematic partial side elevational views of the endoscopic suturing device of FIGS. 1-3, showing successive steps in the operation of the device.

FIG. 7 is a schematic side perspective view of the suture of FIG. 5, upon application to an internal surgical site pursuant to a method in accordance with the present invention.

DETAILED DESCRIPTION OF THE INVENTION

Figure 6C:
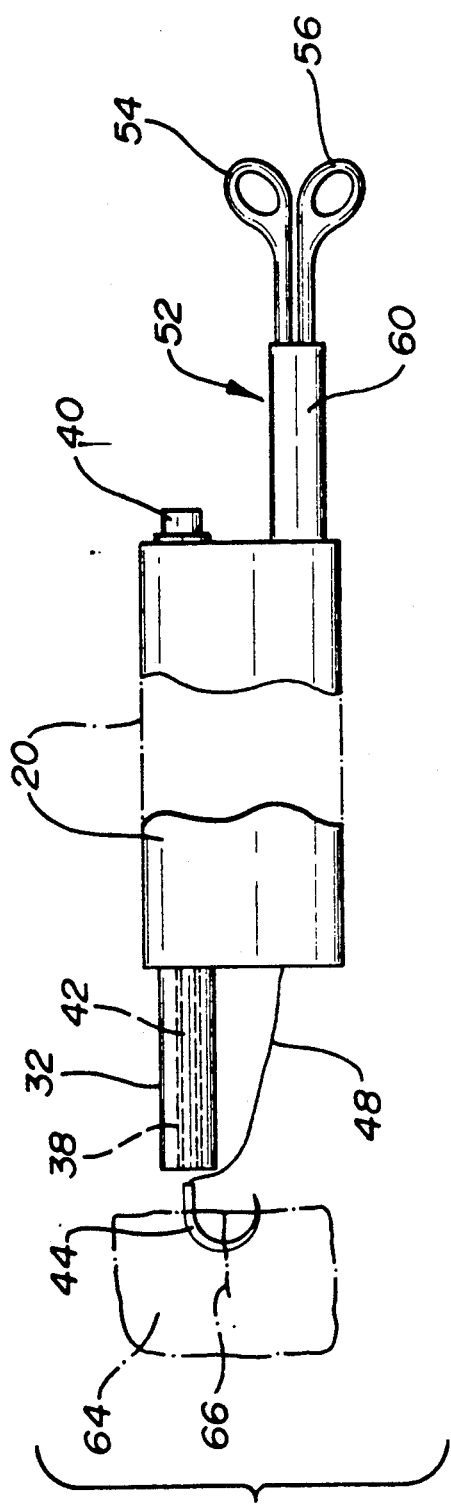

As illustrated in FIGS. 1-3, an endoscopic suturing device comprises an elongate flexible outer tubular endoscope member 20 formed with a biopsy channel 22 extending longitudinally through the tubular member. Biopsy channel 22 includes a first substantially cylindrical portion 24 and a second substantially cylindrical portion 26 each extending the length of tubular member 20 and communicating with one another throughout that length via a connecting channel portion 28. At a proximal end 30, tubular member 20 is connected to conventional endoscope handling devices (not illustrated).

The endoscopic suturing device further comprises an elongate flexible inner tubular member 32 slidably disposed in biopsy channel portion 24. Inner tubular member 32 is provided with a cylindrical bore 34 extending from a proximal end of the tubular member to a shoulder 36 formed near a distal end of member 32. On a distal side of shoulder 36, bore 34 communicates with a thinner cylindrical bore 38 extending from shoulder 36 to the distal end of inner tubular member 32.

The endoscopic suturing device also comprises a cylindrical rod member 40 which is slidably received inside bore 34 of inner tubular member 32. Rod member 40 is provided at a distal end with a cylindrical finger element 42 having a diameter which is less than the diameter of the main body of rod member 40 and less than the diameter of bore 38.

The endoscopic suturing device additionally comprises a needle 44 having a spring bias construction tending to bend needle into an arcuate configuration (see FIG. 2). Needle 44 is made of prestressed nylon or polypropylene or a metal. Needle 44 is loaded into bore 38 of inner tubular member 32 so that the needle is disposed in a straightened configuration in bore 38 distally of a distal end of rod member 40 (see FIG. 3). A suture 46 includes a thread member 48 attached at one end to a loop member 50 and attached at an opposite, free, end to a proximal end of needle 44 (see FIGS. 2 and 3).

The endoscopic suturing device of FIGS. 1-3 includes a a forceps device 52 for closing suture 46 upon an ejection of needle 44 from bore 38 (and hence from biopsy channel portion 24) by a distally directed motion of rod member 40 and upon a subsequent assumption by needle 44 of its prestressed arcuate configuration. Forceps device 52 includes a pair of actuator grips 54 and 56 at a proximal end, a pair of forceps jaws 58 at a distal end, and an elongate flexible body portion 60 slidably inserted through channel portion 26 of endoscope biopsy channel 22.

Inner tubular member 32 and rod member 40 may be provided at a distal end with suitable handgrips (not illustrated) well known to the endoscope arts. The materials of which inner tubular member 32 and rod member 40 are composed enable a sliding fit between those members. In addition, the diameters of inner tubular member 32, rod member 40, and biopsy channel portion 24 are selected in part to facilitate a bending of the endoscope through pathways internal to a patient's body.

To load the endoscopic suturing device of FIGS. 1-3, needle 44 is inserted into the distal end of bore 38, while rod member 40 is inserted into the proximal end of bore 34 up to shoulder 36. Forceps 52 is then inserted through loop member 50 (see FIG. 3) and the assembly including inner tubular member 32, rod member 40, suture 46 and forceps device 52 is then inserted into biopsy channel 22 at the proximal end of outer tubular member 20.

As illustrated in FIG. 4, a suture 110 utilizable as suture 46 comprises a thread member 126, a loop member 124, a connector element or joint portion 114, and inwardly projecting aperture-forming wings 117 and 118 on loop member 124. Suture device 110 further comprises a locking mechanism in the form of a pair of inwardly projecting resilient protuberances 111 and 113 on wings 117 and 118. Thread member 126 is formed along a portion of its length with a series of conically tapering projections 128 and has an outer diameter OD1 defined by a maximum outer transverse dimension of projections 128. Projections 128 each taper from the maximum outer transverse dimension on a side facing joint portion 114 to a minimum traverse dimension at the adjacent projection.

Loop member 124 defines an opening 115 having an effective linear dimension or overall diameter OD2 (when the loop is circularly arranged) substantially larger than outer diameter OD1 of thread member 126. Connector or joint portion 114 serves to couple one end of thread member 126 to loop member 124. Loop member 124, inwardly projecting wings 117 and 118 and protuberances 111 and 113 define a generally oval aperture 116 having a linear dimension or size smaller than outer diameter OD1 of thread member 126. Generally, aperture 116 has an area smaller than the cross-sectional area of projections 128 at the large ends thereof.

Linear dimension or overall diameter OD2 of loop member opening 115 is preferably at least twice as large as outer diameter OD1 of thread member 126. Concomitantly, opening 115 of loop member 124 has an area at least four times the cross-sectional area subtended by projections 128 at their largest width or diameter. This substantial difference in the dimensions of opening 115 and thread member 126 enables practical use of the suture. If opening 115 were smaller, forceps device 52 could would not be able to traverse opening 115.

It is to be noted, however, that loop member opening 115 of suture device 110 has a narrow range of operative sizes. This limitation arises from the fact that loop 124 remains an integral part of the suture after surgery has been completed. For example, if suture device 110 is used to close a tubular body organ such as a blood vessel or bile duct, the circumference of loop member 124 cannot exceed twice the circumference of the vessel or duct.

Protuberances 111 and 113 define a passageway or access channel 120 between opening 115 and aperture 116. The protuberances serve to prevent a removal of thread member 126 from aperture 116 upon a passing of thread member 126 through opening 115 (i.e., through loop member 124) and a subsequent pulling of thread member 126 into aperture 116 from opening 115 through access channel 120.

As shown in FIG. 5, another suture device 210 utilizable as suture 46 in the endoscopic suturing device of FIGS. 1-3 is essentially identical to suture device 210. Suture device 210 comprises a thread member 226, a loop member 224, a connector element or joint portion 214, and inwardly projecting aperture-forming wings 217 and 218 on loop member 224. A pair of inwardly projecting resilient protuberances 211 and 213 are formed on wings 217 and 218 and serve in part to define an aperture 216 at an end of loop member 224 opposite thread member 226. Thread member 226 is formed along a portion of its length with a series of conically tapering projections 228 and has an outer diameter OD1' defined by a maximum outer transverse dimension of projections 228. Projections 228 each taper from the maximum outer transverse dimension on a side facing joint portion 214 to a minimum traverse dimension at the adjacent projection.

Loop member 224 defines an opening 215 having an effective linear dimension or overall diameter OD2' (when the loop is circularly arranged) substantially larger than outer diameter OD1' of thread member 226. In contrast, aperture 216 has a linear dimension or size smaller than outer diameter OD1' of thread member 226. Generally, aperture 216 has an area smaller than the cross-sectional area of projections 228 at the large ends thereof.

Projections 228 are thin walled and generally collapse to a closed configuration shown at 229 in FIG. 5. In that closed configuration, projections 228 form a smooth surface when rubbed from the free end of thread member 226 towards loop member 224. Projections 228 expand into a locking, opened configuration shown at 231 upon the application of a force directed along thread member 226 from loop member 224 towards the free end of the thread member.

Suture devices 110 and 210 are integrally molded pursuant to techniques well known in the art. The sutures are made of polyethylene, polypropylene, nylon, tetrafluoroethylene or other synthetic resin or polymeric material which is essentially inert and therefore biochemically safe for sustained contact with the body tissues of human beings and other animals. Needle 44 is similarly made of a biologically inert material Needle 44 is attached to the free ends of thread members 126 and 226 by embedding techniques also well known in the art.

It is to be noted that loop members 124 and 224 are made of a flexible, thin, thread-like element. The thin thread-like element enables loop members 124 and 224 to be wound about a body tissue such as a blood vessel or duct. Thus, the flexibility of the loop members enables suture 110 or 210 to conform to the body tissues to which it is attached.

As shown in FIG. 6A, upon an insertion of a distal end of the endoscopic suturing device of FIGS. 1-3 into a patient's body (not shown), light 62 is emitted from the distal end of outer tubular member 20 and illuminates tissues 64 at an internal surgical site including a wound 66. Light 68 is reflected from the tissues 64 and is directed through an optical fiber or group of fibers 70 to an eyepiece (not shown) or camera (not illustrated) from whence a video picture is produced on a display screen (not depicted). A surgeon visually inspects the surgical site through the medium of the transmitted optical radiation and determines the location of wound 66. The operating surgeon manipulates the endoscope to position the distal end of outer tubular member 20 optimally with respect to the surgical site.

Upon the proper positioning of the distal end of outer tubular member 20, inner tubular member 32, together with entrained rod member 40 and suture 46, is shifted longitudinally through biopsy channel portion 24 in the distal direction until a distal tip of the inner tubular member is juxtaposed to tissues 64, as shown in FIG. 6B. In a subsequent step of an operating procedure in accordance with the invention, illustrated in FIG. 6C, rod member 40 is shifted distally relative to inner tubular member 32 so that finger element 42 enters bore 38 and ejects needle 44 therefrom. Upon ejection of needle 44, it assumes its prestressed arcuate configuration, as shown in FIG. 6C. The needle thus pierces internal body tissues 64 on both sides of wound 66.

Figure 6D:
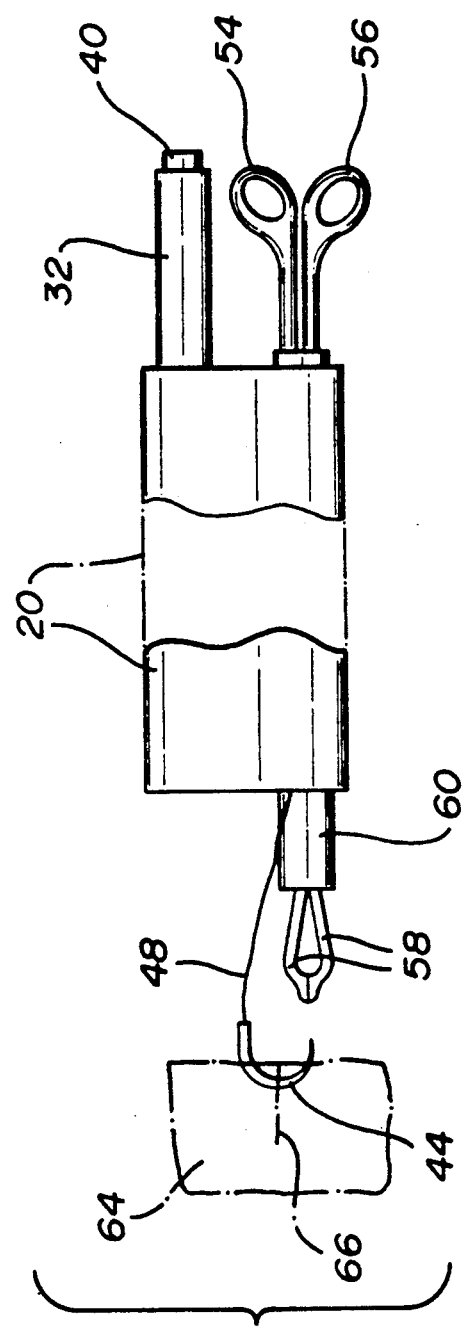
Figure 6E:
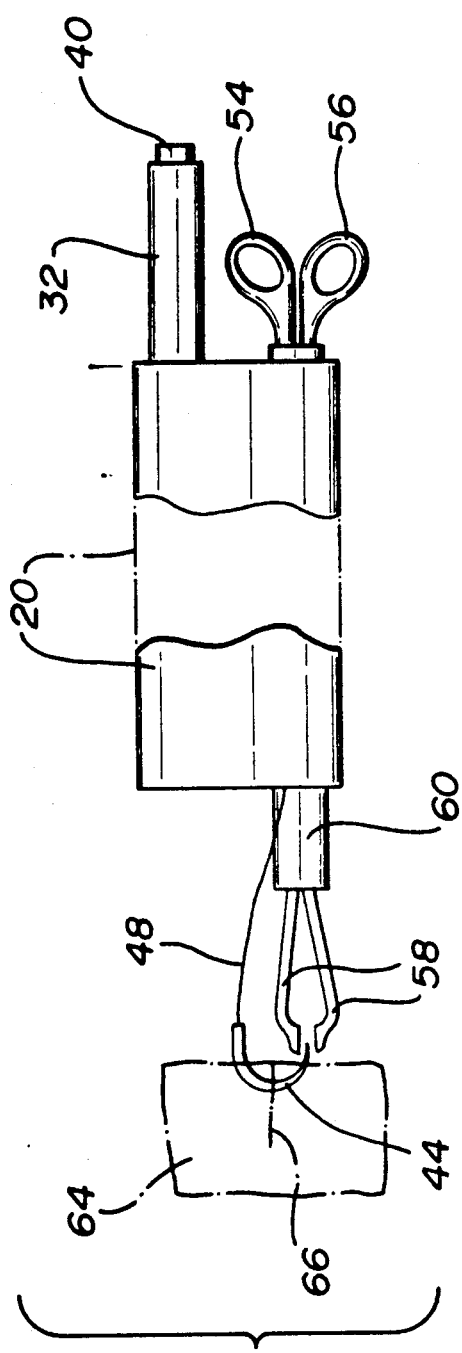

Upon a piercing of tissues 64 by needle 44, the operating surgeon slides inner tubular member 32, with entrained rod member 40, back into a withdrawn position (see FIG. 6D) and translates forceps device 52 distally so that forceps jaws 58 are juxtaposed to the protruding front end of needle 44. The surgeon then actuates grips 54 and 56 to open jaws 58 (FIG. 6E). The entire endoscopic suturing device or, alternatively, forceps device 52 may subsequently be shifted further in the distal direction, if necessary, so that the protruding tip of needle 44 is disposed between the separated jaw members 58 (FIG. 6E).

Figure 6F:
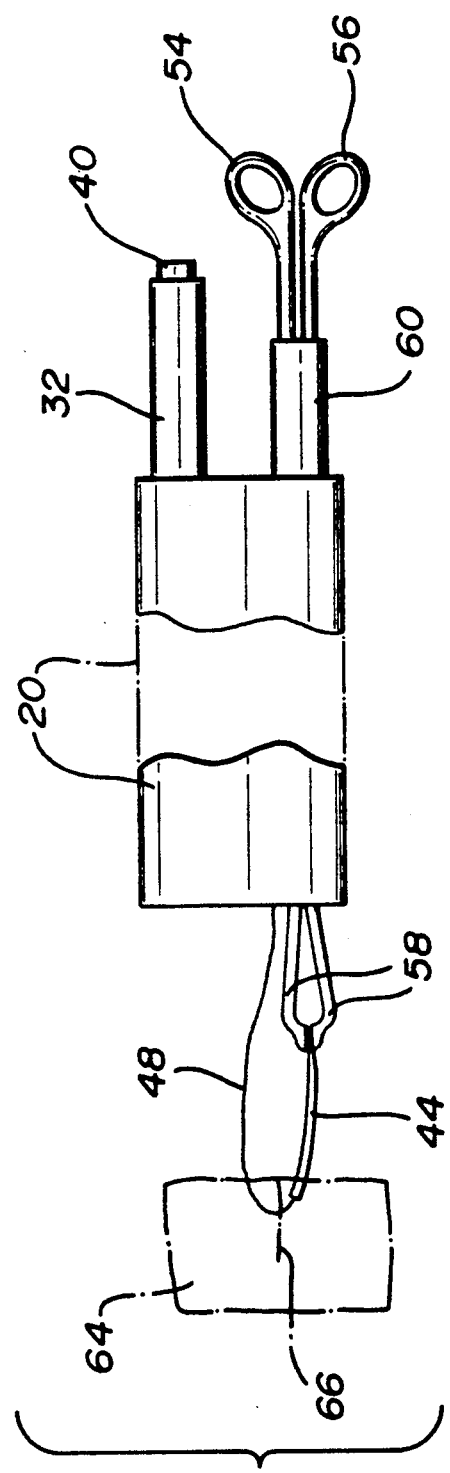

As depicted in FIG. 6F, the operating surgeon actuates grips 54 and 56 to close forceps jaws 58 upon visually detecting through the optical assembly of the endoscope that the protruding free end of needle 44 is located between the jaws. Upon a gripping of needle 44 by jaws 58, the surgeon pulls forceps device 52 in the proximal direction. During this pulling step (FIGS. 6F and 6G), thread member 48 is pulled in the proximal direction, thereby moving loop member 50 in the distal direction.

Upon a pulling of thread member 48 through the aperture (116 or 216) of suture 46 and a locking of the suture device via the projections (128 or 228) on the thread member, the operating surgeon inserts a cutting device such as a laser transmitting fiber 72 (FIG. 6H) through another biopsy channel 74 (FIGS. 1 and 2) in outer tubular member 20 and manipulates the laser fiber so that a distal, output, end thereof is justaposed to thread member 48 at loop member 50. A laser source 76 is subsequently energized or activated to transmit a beam of radiation through fiber 72 to sever thread member 48.

FIG. 7 shows the suture 210 of FIG. 5 in place in tissues 64 and binding wound 66 upon a severing of thread member 226 by a laser beam transmitted from laser source 76 via fiber 72 (FIG. 6H) or by another alternatively utilizable cutting instrument such as an endoscopic scalpel or scissors device. A portion of thread member 226 traverses aperture 216 and is locked into position by the cooperation of protuberances 211 and 213 and an expanded projection 228, the other projections along thread member 226 remaining in a collapsed or closed configuration.

An endoscopic suturing device in accordance with the principles of the invention may include a pair of forceps devices insertable through biopsy channel portions 24 and 26. Such an endoscopic suturing device is particularly adapted to ligating tubular body organs such as blood vessels, bile ducts and Fallopian tubes. Such a device uses a suture device as described herein, with the loop member of the suture device being traversed by one of the forceps devices.

Bore 38 (see FIGS. 2 and 3) may be provided at a distal end with a pair of diametrically opposed longitudinally extending grooves (not illustrated) for receiving portions of needle 44 and guiding the needle during an ejection step. The grooves or other orientation device thus serves to control the disposition of needle 44 in tissues 64 or about a tubular internal body organ during a suturing or ligating operation.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A surgical instrument comprising:
   an endoscope including an elongate flexible outer tubular member and a biopsy channel extending longitudinally through said tubular member;
   an elongate flexible rod member slidably disposed inside said biopsy channel;
   a needle having a spring bias construction tending to bend said needle into an arcuate configuration, said needle being disposed in a straightened configuration at least partially inside said biopsy channel distally of a distal end of said rod member;
   a suture having an end attached to a proximal end of said needle; and
   means for closing said suture upon an ejection of said needle from said biopsy channel by a distally directed motion of said rod member and a subsequent assumption by said needle of said arcuate configuration.

2. The surgical instrument set forth in claim 1, further comprising an elongate flexible inner tubular member slidably disposed in said biopsy channel, said rod member being slidably disposed inside said inner tubular member, said needle being disposed in a straightened configuration at least partially inside said inner tubular member distally of a distal end of said rod member.

3. The surgical instrument set forth in claim 2 wherein said biopsy channel includes a pair of parallel elongate main channel portions communicating with one another along their lengths via an elongate connecting channel portion.

4. The surgical instrument set forth in claim 3 wherein said inner tubular member is slidably disposed in one of said main channel portions.

5. The surgical instrument set forth in claim 4 wherein said means for closing includes an elongate flexible forceps member slidably disposed in the other of said main channel portions.

6. The surgical instrument set forth in claim 5 wherein said suture includes a loop member traversed by said elongate flexible forceps member, said suture further including a thread member attached at one end to said needle and at an opposite end to said loop member, said thread member traversing said connecting channel portion.

7. The surgical instrument set forth in claim 6, further comprising means for locking said suture upon closure thereof by said means for closing.

8. The surgical instrument set forth in claim 6 wherein said means for locking includes a series of projections provided along said thread member and an aperture in said suture communicating with an opening defined by said loop member, said thread member having an outer diameter defined by said projections, said opening having a linear dimension substantially larger than said outer diameter, said aperture having a linear dimension smaller than said outer diameter, said means for locking further including means on said suture for preventing a removal of said thread member from said aperture upon a passing of said thread member through said loop member and a subsequent pulling of said thread member into said aperture from said loop member.

9. The surgical instrument set forth in claim 5 wherein said rod member, said inner tubular member, said forceps member, and said main channel portions are all substantially cylindrical.

10. The surgical instrument set forth in claim 2, further comprising arrest means for preventing said rod member from moving more than a predetermined distance in a distal direction relative to said inner tubular member.

11. The surgical instrument set forth in claim 10 wherein said arrest means includes a shoulder on said rod member engageable with a shoulder internal to said inner tubular member.

12. The assembly set forth in claim 16 wherein said arrest means includes a shoulder on said rod member engageable with a shoulder internal to said tubular member.

13. The surgical instrument set forth in claim 1, further comprising means for severing a portion of said suture upon a closing thereof.

14. The surgical instrument set forth in claim 13 wherein said means for severing includes a laser device with an optical fiber insertable through a longitudinal opening in said outer tubular member.

15. A surgical suturing assembly comprising:
   an elongate flexible tubular member having a diameter sufficiently small so that said tubular member is slidably insertable into a biopsy channel extending longitudinally through a flexible tubular endoscope member;
   an elongate flexible rod member slidably disposed inside said elongate flexible tubular member;
   a needle having a spring bias construction tending to bend said needle into an arcuate configuration, said needle being disposed in a straightened configuration at least partially inside said tubular member distally of a distal end of said rod member; and
   a suture having an end attached to a proximal end of said needle.

16. The assembly set forth in claim 15, further comprising means for closing said suture upon an ejection of said needle from said tubular member by a distally directed motion of said rod member and a subsequent assumption by said needle of said arcuate configuration.

17. The assembly set forth in claim 16 wherein said means for closing includes an elongate flexible forceps member.

18. The assembly set forth in claim 17 wherein said suture includes a loop member traversed by said elongate flexible forceps member, said suture further including a thread member attached at one end to said needle and at an opposite end to said loop member.

19. The assembly set forth in claim 18, further comprising means for locking said suture upon closure thereof by said means for closing.

20. The assembly set forth in claim 19 wherein said means for locking includes a series of projections provided along said thread member and an aperture in said suture communicating with an opening defined by said loop member, said thread member having an outer diameter defined by said projections, said opening having a linear dimension substantially larger than said outer diameter, said aperture having a linear dimension smaller than said outer diameter, said means for locking further including means on said suture for preventing a removal of said thread member from said aperture upon a passing of said thread member through said loop member and a subsequent pulling of said thread member into said aperture from said loop member.

21. The assembly set forth in claim 15 wherein said rod member and said tubular member are cylindrical.

22. The assembly set forth in claim 15, further comprising arrest means for preventing said rod member from moving more than a predetermined distance in a distal direction relative to said tubular member.

23. A surgical instrument comprising:
an endoscope including an elongate flexible outer tubular member and a biopsy channel extending longitudinally through said tubular member;
a needle having a spring bias construction tending to bend said needle into an arcuate configuration, said needle being disposed in a straightened configuration at least partially inside said biopsy channel at a distal end thereof;
means for ejecting said needle from said biopsy channel;
a suture having an end attached to a proximal end of said needle; and
means for closing said suture upon an ejection of said needle from said biopsy channel by a distally directed motion of said rod member and a subsequent assumption by said needle of said arcuate configuration.

24. The surgical instrument set forth in claim 23 wherein said means for ejecting includes an elongate flexible rod member slidably disposed inside said biopsy channel.

25. The surgical instrument set forth in claim 24 wherein said means for ejecting further includes an elongate flexible inner tubular member slidably disposed in said biopsy channel, said rod member being slidably disposed inside said inner tubular member, said needle being disposed in a straightened configuration at least partially inside said inner tubular member distally of a distal end of said rod member.

26. The surgical instrument set forth in claim 23 wherein said means for closing includes an elongate flexible forceps member slidably disposed in said endoscope.

27. The surgical instrument set forth in claim 26 wherein said suture includes a loop member traversed by said elongate flexible forceps member, said suture further including a thread member attached at one end to said needle and at an opposite end to said loop member.

28. The surgical instrument set forth in claim 23, further comprising means for locking said suture upon closure thereof by said means for closing.

29. The surgical instrument set forth in claim 28 wherein said means for locking includes a series of projections provided along said thread member and an aperture in said suture communicating with an opening defined by said loop member, said thread member having an outer diameter defined by said projections, said opening having a linear dimension substantially larger than said outer diameter, said aperture having a linear dimension smaller than said outer diameter, said means for locking further including means on said suture for preventing a removal of said thread member from said aperture upon a passing of said thread member through said loop member and a subsequent pulling of said thread member into said aperture from said loop member.

30. The surgical instrument set forth in claim 23, further comprising means for severing a portion of said suture upon a closing thereof.

31. A suture device comprising:
a thread member provided along at least a portion of its length with a series of resilient projections, said thread member having an outer diameter defined by said projections;
a loop member defining an opening having a linear dimension substantially larger than said outer diameter; and
joining means for connecting one end of said thread member to said loop member, at least one of said joining means and said loop member defining at least in part an aperture having a linear dimension smaller than said outer diameter, said aperture communicating with said opening defined by said loop;
locking means, provided on at least one of said joining means and said loop member, for preventing a removal of said thread member from said aperture upon a passing of said thread member through said loop member and a subsequent pulling of said thread member into said aperture from said loop member; and
a needle having a spring bias construction tending to bend said needle into an arcuate configuration, said needle having a sharp end and being attached at an opposite end to a free end of said thread member.

32. The suture device set forth in claim 31 wherein said aperture is formed on said loop member at a point therealong spaced from said joining means.

33. The suture device set forth in claim 31 wherein said locking means includes at least one protuberance on said loop.

34. The suture device set forth in claim 33 wherein said protuberance projects towards said aperture.

35. The suture device set forth in claim 34 wherein said protuberance is undercut on a side facing said aperture.

36. The suture device set forth in claim 31 wherein said joining means comprises a Y-shaped connector piece between said one end of said thread member and said loop member.

37. The suture device set forth in claim 31 wherein said projections are tapered from a larger transverse dimension down towards an end of said thread member opposite said joining means.

38. The suture device set forth in claim 31 wherein said projections are substantially hollow.

39. A suture device comprising:
a thread member provided along at least a portion of its length with a series of resiliently collapsible projections, said thread member having an outer diameter defined by said projections;

a loop member defining an opening having a linear dimension substantially larger than said outer diameter;

joining means for connecting one end of said thread member to said loop member, at least one of said joining means and said loop member defining at least in part an aperture having a linear dimension smaller than said outer diameter, said aperture communicating with said opening defined by said loop;

locking means, provided on at least one of said joining means and said loop member, for preventing a removal of said thread member from said aperture upon a passing of said thread member through said loop member and a subsequent pulling of said thread member into said aperture from said loop member; and a needle having a spring bias construction tending to bend said needle into an arcuate configuration, said needle having a sharp end and being attached at an opposite end to a free end of said thread member.

40. The suture device set forth in claim 39 wherein said projections are collapsible under force applied along said thread member in one direction and expandable under force applied along said thread member in an opposite direction.

41. The suture device set forth in claim 40 wherein said projections are substantially hollow conical elements.

42. A surgical needle having a spring bias construction tending to bend said needle into an arcuate configuration, said needle being bendable into a straightened configuration, said needle having a sharp tip at one end, said needle being provided at an opposite end with means for attaching said needle to a suture.

43. A method for performing a surgical operation on internal body tissues of a patient, comprising the steps of:

inserting a tubular endoscope member through an aperture in the patient's body;

using said endoscope to visually locate the internal body tissues inside the patient's body;

upon locating said surgical site, pushing an elongate flexible rod member in a distal direction through a biopsy channel in said tubular endoscope member to eject a needle disposed in a straightened configuration inside said channel at a distal end of said tubular endoscope member, said needle having a spring bias construction tending to bend said needle into an arcuate configuration, said needle having a proximal end attached to a suture;

upon ejection of said needle from said channel, passing said needle in said arcuate configuration through the internal body tissues;

upon passing of said needle through the internal body tissues, closing said suture; and upon closure of said suture, withdrawing said tubular endoscope member out of the patient's body though said aperture.

44. The method set forth in claim 43 wherein said needle has a sharp end opposite said proximal end and wherein said suture has a thread member and a loop member attached to said thread member at an end thereof opposite said needle, said step of closing comprising the steps of grasping said sharp end and pulling said needle and a portion of said thread member through said loop member.

45. The method set forth in claim 44 wherein said step of grasping includes the step of operating a forceps device.

46. The method set forth in claim 45 wherein said step of pulling comprises the step of pulling a portion of said forceps device through said loop member.

47. The method set forth in claim 43, further comprising the step of locking said suture in a closed configuration upon closure of said suture.

48. The method defined in claim 43 wherein said aperture is a natural body opening.

49. The method defined in claim 43, further comprising the step of piercing the patient's body to form said aperture.

50. The method defined in claim 49 wherein said step of piercing is performed by using a trocar.

51. A surgical instrument comprising:

an endoscope including an elongate flexible outer tubular member and a first biopsy channel and a second biopsy channel both extending longitudinally through said tubular member, said outer tubular member being formed with an elongate connecting channel connecting said first biopsy channel to said second biopsy channel along their lengths;

a suture device comprising
a thread member provided along at least a portion of its length with a series of resilient projections, said thread member having an outer diameter defined by said projections;

a loop member defining an opening having a linear dimension substantially larger than said outer diameter; and joining means for connecting one end of said thread member to said loop member, at least one of said joining means and said loop member defining at least in part an aperture having a linear dimension smaller than said outer diameter, said aperture communicating with said opening defined by said loop;

locking means, provided on at least one of said joining means and said loop member, for preventing a removal of said thread member from said aperture upon a passing of said thread member through said loop member and a subsequent pulling of said thread member into said aperture from said loop member; and a first elongate flexible member slidably inserted in said first biopsy channel, said first elongate flexible member including holding means at a distal end for holding said thread member of said suture device; and a second elongate flexible member slidably inserted in said second biopsy channel, said second elongate flexible member being provided at a distal end with grasping means for grasping a free end of said thread member upon a moving of at least an end portion of said thread member out from said first biopsy channel upon a distally directed motion of said first elongate flexible member, said loop member being traversed in said second biopsy channel by said second elongate flexible member, said thread member extending from said loop member through said connecting channel to said first biopsy channel.

* * * * *